United States Patent [19]

Osbon et al.

[11] Patent Number: 5,083,556
[45] Date of Patent: Jan. 28, 1992

[54] PENILE CINCTURE BAND OPERATIONAL APPARATUS

[75] Inventors: Julian W. Osbon; Eugene H. Parker, both of Augusta, Ga.; Philip L. Reid, Duncan, S.C.

[73] Assignee: Osbon Medical Systems, Ltd., Augusta, Ga.

[21] Appl. No.: 531,518

[22] Filed: May 31, 1990

[51] Int. Cl.⁵ .................................................. A61F 5/41
[52] U.S. Cl. ........................................ 128/79; 606/141
[58] Field of Search .................. 128/79; 606/140, 141, 606/157

[56] References Cited

U.S. PATENT DOCUMENTS

| | | | |
|---|---|---|---|
| D. 293,473 | 12/1987 | Chaney | D24/64 |
| 823,877 | 6/1906 | Kellogg | 606/140 |
| 2,619,964 | 12/1952 | Thaete | 606/140 |
| 2,764,160 | 9/1956 | Alexander et al. | 128/303 |
| 2,942,604 | 6/1960 | Gravlee, Jr. | 128/303 |
| 3,382,873 | 5/1968 | Banich et al. | 128/326 |
| 3,726,278 | 4/1973 | Scott | 606/140 |
| 3,760,810 | 9/1973 | Van Hoorn | 606/140 |
| 3,989,049 | 11/1976 | Yoon | 128/326 |
| 4,257,419 | 3/1981 | Goltner et al. | 128/303 A |
| 4,291,451 | 9/1981 | O'Neill et al. | 29/235 |
| 4,378,008 | 3/1983 | Osbon, Sr. | 128/79 |
| 4,493,319 | 1/1985 | Polk et al. | 128/303 A |
| 4,539,980 | 9/1985 | Chaney | 128/79 |
| 4,548,201 | 10/1985 | Yoon | 128/326 |
| 4,553,300 | 11/1985 | Mancha | 29/235 |
| 4,628,915 | 12/1986 | Chaney | 128/79 |
| 4,741,329 | 5/1988 | Marcune | 128/79 |
| 4,856,498 | 8/1989 | Osbon | 128/79 |

Primary Examiner—Cary E. O'Connor
Attorney, Agent, or Firm—Dority & Manning

[57] ABSTRACT

A cone-shaped expansion member has an axially facing curved lip for alternative engagement with the entrance end of a penile vacuum chamber or an annular transfer collar. A plurality of interference engagement struts extend in an axial direction from the base of the cone member, for removable interference engagement of the cone with a vacuum chamber or transfer collar. The transfer collar is adapted to be slipped over the user's male sex organ with an enlarged cincture band received thereabout, so that such cincture band may be applied to the base of the user's male sex organ for securing an engorged condition thereof. The transfer collar permits subsequent use of a preexpanded resilient cincture band. When the cone is directly applied to the entrance end of a vacuum chamber, a resilient cincture band may be enlarged by application of same against the cone and directly received about the outside diameter of such vacuum chamber for subsequent application to the base of the user's male sex organ.

17 Claims, 2 Drawing Sheets

PENILE CINCTURE BAND OPERATIONAL APPARATUS

BACKGROUND OF THE INVENTION

The present application concerns apparatus for resilient penile cincture band operations in general, and more particularly, a device for expansion of a resilient penile cincture band and subsequent transfer thereof.

The problem of male impotence (i.e., the inability to gain an adequate penile erection for coitus) is well known and the subject of considerable scientific and medical activity. Various surgical and nonsurgical therapies are available for treatment of male impotence. One therapy makes use of a vacuum chamber device for producing penile engorgement and rigidity by drawing blood into the erectile bodies of the user's male sex organ, i.e.. the penis. The subject's penis is placed within a vacuum chamber or cylinder for producing engorgement which condition may typically be subsequently secured with an elastic cincture band or the like.

U.S. Pat. Nos. 4,378,008 (Osbon, Sr.) and 4,856,498 (Osbon) disclose examples of vacuum chambers for use in conducting vacuum erection enhancement therapy. Also illustrated are examples of elastic bands or cincture rings for securing an engorged condition. The disclosures of both such patents are hereby incorporated herein by reference. In general, such cincture bands are enlarged and placed as shown about the distal or open entrance end of the vacuum chamber so as to be readily advanced onto the base of the user's male sex organ after its engorgement. Both such patents, as well as U.S. Pat. No. 293,473 (Chaney) and U.S. Pat. No. 4,539,980 (Chaney) disclose examples of resilient penile cincture bands, both with and without handles.

One of the known somewhat problematic aspects of utilizing vacuum erection enhancement therapy concerns the simple necessity of handling the apparatus itself. Because of the relatively small size of the resilient penile cincture band, the relatively high resiliency thereof, and the acts involved in its use, some degree of user strength and dexterity is involved with its placement and with practice of the overall therapy. Of course, the degree of "difficulty" encountered by each user at a given time tremendously varies subject to numerous highly subjective factors and considerations. Such is equally true whenever a cincture band is utilized for securing an engorged penile condition, regardless of whether vacuum therapy is used to induce such condition, or if other methods or techniques are used.

U.S. Pat. Nos. 4,539,980 and 4,628,915 (Chaney) disclose an accessory generally for use in expanding an elastic ring for contracting on the penis to maintain an erection. As illustrated for example in FIG. 5 of the '980 patent and FIG. 2 of the '915 patent, a cone portion is integrally formed with a cylindrical portion which removably receives a sleeve thereover. The sleeve is secured by fitting of a tapered pin, for example such as a spring-loaded spindle or the like, which is associated with an exposed portion of the cylindrical region after passage of the sleeve thereover. The small end of the cone is closed, and a number of separate parts are required for temporarily securing the removable sleeve along the length of the cylindrical portion and relative the cone for receiving an expanded elastic ring therefrom.

SUMMARY OF THE INVENTION

The present invention recognizes and addresses various of the foregoing problems, and others, concerning elastic penile cincture band operations. Thus, broadly speaking, a present main object is improved penile elastic cincture band operations. More particularly, a present main concern is improved cincture band handling operations, such as expansion of an elastic band and/or subsequent transference thereof to another structure such as either a vacuum chamber erection device or an intermediate transfer collar.

It is another more particular object of the present invention to provide improved apparatus for expanding an elastic penile cincture band, including simple and ready construction thereof and subsequent maintenance (i.e.. cleansing and the like) thereof.

It is yet another more particular present object to provide such an improved apparatus which further facilitates subsequent transference of the expanded band directly onto the outside diameter of a vacuum generating penile erection chamber or to the outside diameter of a transfer collar for subsequent application to the base of a user's male sex organ.

Still a further present broad object is to provide improved apparatus for expansion and/or other handling of a resilient cincture band, for ease of the patient's use, thereby improving efficiency of and confidence in the associated impotence therapy.

It is another more particular object to provide such improved apparatus usable with either vacuum erection enhancement therapy, or usable with other engorgement producing techniques for subsequent securement of an engorged condition with a resilient penile cincture band.

Additional objects and advantages of the invention are set forth, or will be apparent to those of ordinary skill in the art, from the detailed description which follows. Also, it should be appreciated that modifications and variations to the specifically illustrated and discussed features hereof may be practiced in various embodiments and uses of this invention without departing from the spirit and scope thereof, by virtue of present reference thereto. Such variations may include, but are not limited to, substitution of equivalent means and features (or materials) for those shown or discussed, and the functional or positional reversal of various parts or features, or the like.

Still further, it is to be understood that different embodiments, as well as different presently preferred embodiments, of this invention may include various combinations of presently disclosed features, or their equivalents (including combinations thereof not expressly shown or stated). One exemplary such embodiment of the present invention relates to an apparatus for expanding an elastic penile cincture band to be subsequently applied to the outside diameter of a vacuum generating penile erection chamber or the base of a user's male sex organ. Such apparatus comprises a generally conical enlargement member and a plurality of struts extending therefrom. The enlargement member has a relatively small diameter end and opposite thereto a relatively enlarged diameter base, with a tapered outside diameter between such end and such base. The struts extend from the conical enlargement member base and are adapted to alternatively engage the inside diameter of one of the entrance end of a vacuum generating penile erection chamber and a transfer collar for subsequent application to the base of a user's male sex organ. With such apparatus, an elastic penile cincture band may be readily expanded by its application against the tapered outside diameter and subsequently used to secure an engorged condition of a user's male sex organ.

Another present exemplary embodiment also relates to a device for expanding an elastic penile cincture band and facilitating transfer of the expanded band to a further structure for subsequent use in securing an engorged condition of a user's penis. Such device includes cones means and interference engagement means. The cone means preferably has a tapered end and a relatively enlarged circular base which terminates in a curved and generally axially facing lip. Such cone means are for expanding a resilient penile cincture band applied to the tapered end thereof and advanced towards the relatively enlarged circular base. The interference engagement means are preferably supported on the cone means and project generally axially therefrom. Such interference engagement means are for removably engaging the cone means with a further structure such as a penile vacuum chamber or an annular transfer collar. Such further structure has an engagement edge thereof received against the cone means axially facing lip, so that a resilient penile cincture band may be readily expanded by the cone means and transferred to the further structure temporarily associated therewith by the interference engagement means.

Yet another construction comprising a present exemplary embodiment includes a device for facilitating expansion of a resilient penile cincture band and subsequent transference thereof to the base of a user's penis for securing an engorged penile condition. Such construction preferably includes a hollow conical member, a plurality of engagement members, and an annular transfer collar.

In the foregoing exemplary device, the hollow conical member has a relatively enlarged circular base tapering in an axial direction of the member to a relatively smaller end, with openings defined in such base and such end to facilitate cleansing of the member interior. The member further has a curved, axially facing engagement lip defined in its circular base. The plurality of engagement members are preferably integrally formed with the interior of the hollow conical member and extending in a generally axial direction from the base thereof.

The foregoing annular transfer collar preferably has an inside diameter adapted for a removable interference fit about the above-referenced engagement members, and has a curved engagement edge adapted for fitting to the conical member circular base engagement lip so that a resilient cincture band slipped over the conical member relatively smaller end and advanced towards the base thereof may be expanded for transfer to the annular transfer collar. After such operation, the collar may be selectively removed from the interference fit with the engagement members with the expanded band thereabout and slipped over a user's penis for securement of an engorged condition thereof by applying the expanded band to the base of the penis.

In the foregoing exemplary devices, the annular transfer collar may further include a relatively reduced outside diameter portion for reducing the requisite contraction distance of the expanded band during its application to the user's penis, thereby reducing discomfort to the user during such application.

In still further embodiments of the present invention, a device such as above may be used separate and apart from an annular transfer collar. In such instances, the device is preferably adapted for forming a removable interference fit with the entrance end of a penile vacuum chamber so that a cincture band may be expanded and transferred directly to the outside diameter of such vacuum chamber for subsequent application to the base of a user's penis to secure an engorged condition thereof obtained with such vacuum device.

Those of ordinary skill in the art will better appreciate the features and aspects of such embodiments, and others, upon review of the remainder of the specification.

BRIEF DESCRIPTION OF THE DRAWINGS

A full and enabling disclosure of the present invention, including the best mode thereof, directed to one of ordinary skill in the art, is set forth in the remainder of the specification, which makes reference to the appended figures, in which.

Figure 1:
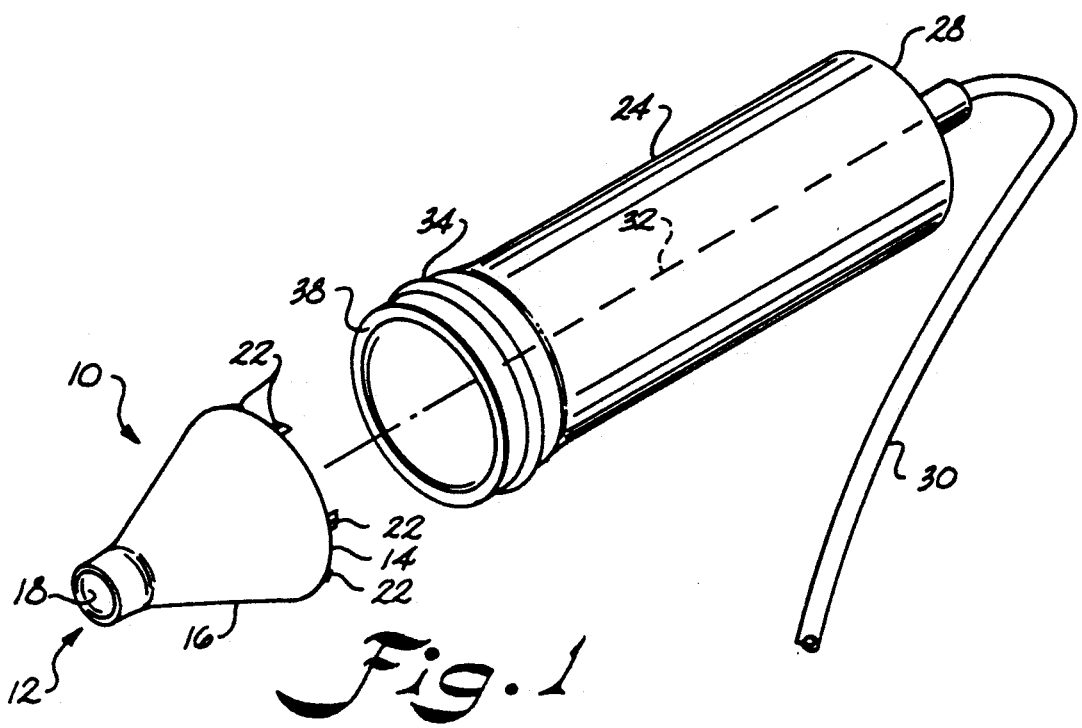
FIG. 1 is a generally side and top perspective view of a first embodiment in accordance with this invention, associated with a vacuum generating penile erection chamber.

Repeat use of reference characters throughout the present specification and appended drawings is intended to represent same or analogous features or elements of the invention.

DETAILED DESCRIPTION OF THE PREFERRED EMBODIMENTS

Figure 2:
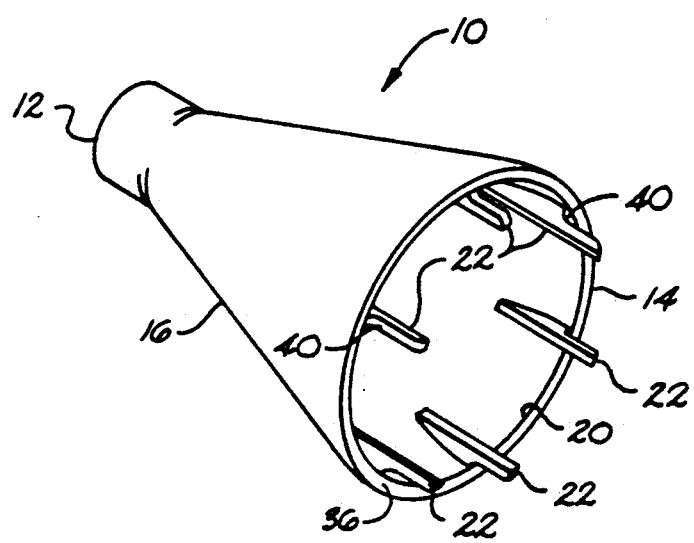
FIG. 2 is an enlarged generally side and bottom perspective view of the exemplary embodiment of present FIG. 1.

FIGS. 1 and 2 illustrate the first of several presently preferred embodiments of apparatus for expanding an elastic penile cincture band to be subsequently applied to the outside diameter of a vacuum generating penile erection chamber (or alternatively to the base of a user's male sex organ). A generally conical enlargement member or cone means 10 has a relatively small diameter or tapered end 12, and opposite thereto has a relatively enlarged diameter generally circular base 14. FIGS. 1 and 2 are both perspective views, but tilted respectively to show primarily ends 12 and 14.

Figures 3, 4:
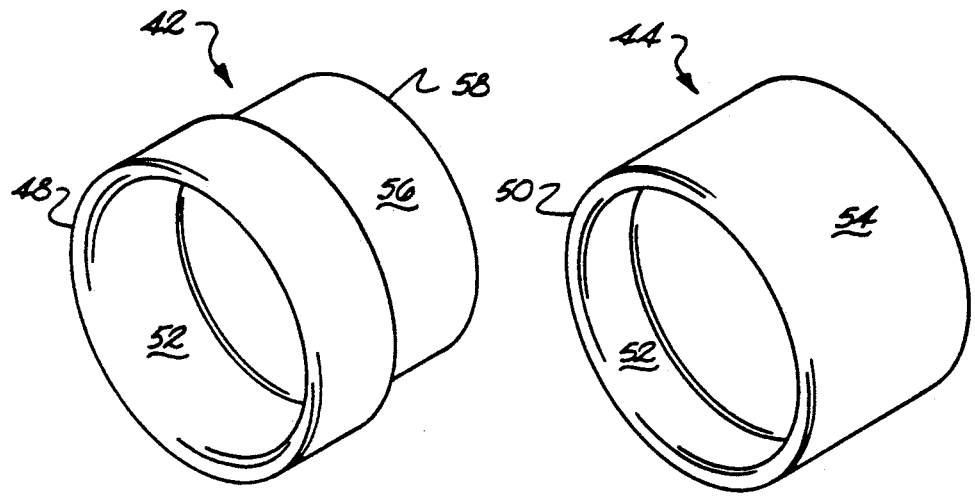
FIGS. 3 and 4 illustrate respective alternative embodiments in accordance with this invention of present annular transfer collars, which in respective combinations with the present embodiment of FIG. 2 form further exemplary embodiments in accordance with this invention.

Cone means or conical member 10 further defines a tapered outside diameter 16 between its respective ends 12 and 14. As should be apparent to those of ordinary skill in the art, a resilient cincture band passed over relatively smaller end 12 and advanced towards end 14 against outside diameter 16, will be enlarged to the diameter defined by end 14. Generally, some form of lubricant is preferred to assist in such advancement. Also, it should be appreciated that the above-described apparatus may be used in association with different forms of resilient cincture bands. FIG. 4 of above-reference U.S. Pat. No. 4,856,498 is an example of one suitable elastic constriction band, made for materials such as natural latex rubber, and having handle means or the like formed therewith to facilitate their usage. Conical member 10 is preferably formed of substantially rigid material, such as plastics.

As illustrated, cone means 10 is preferably generally hollow and defines openings 18 and 20 in its respective ends 12 and 14. Such overall construction facilitates cleansing of member 10, since its entire interior is substantially exposed. The ready ability to thoroughly clean member 10 contributes to overall good hygienic habits concerning usage of constriction band technology. Additionally, construction of cone means 10 is facilitated where a generally hollow body with openings on each end is provided, particularly where construction is of plastic material.

The exemplary apparatus of present FIGS. 1 and 2 further includes a plurality of struts 22 which function as interference engagement means for removably engaging member 10 with a further structure such as a penile vacuum chamber 24. Struts 22 extend from the conical enlargement member base 14, and are preferably integrally formed, such as from plastic material, with member 10. As represented in present FIG. 2, such struts in this particular preferred embodiment are preferably six in number, and are spaced relatively equi-distantly about the circumference of base 14. Other numbers and placements of struts may be practiced for comprising interferencing engagement means in accordance with this invention.

By virtue of their positioning, struts 22 may form a slight interference fit with a generally circular opening, such as formed by the entrance end 26 of vacuum chamber 24. Such chamber 24 is a general representation of typical penile vacuum chambers, having a generally open entrance end 26 for entrance and receipt of a user's male sex organ into chamber 24. A generally closed end 28 is typically fitted with a tubing 30 or the like through which chamber 24 is at least partially evacuated for producing engorgement of an organ received therein. Various devices, such as vacuum pumps, hand pumps, or the like, may be used in association with tubing 30, details of which form no particular aspect of the present invention.

In accordance with this invention, cone means 10 is aligned as illustrated in present FIG. 1 so that the lengthwise axis thereof is substantially co-axial with the lengthwise axis 32 of chamber 24. Struts 22 are then inserted into entrance end 26 so as to form a slight interference fit therewith. Once base 14 is suitable received against entrance end 26 of chamber 24, an elastic constriction band or penile cincture band 34 may be placed over end 12 and advanced towards base 14. Such advancement continues until band 34 is fully enlarged and transferred onto the outside diameter of chamber 24 adjacent end 26 thereof, a position which exemplary band 34 occupies in the illustration of present FIG. 1. Thereafter, conical member 10 may be withdrawn or disconnected from chamber 24. Constriction band 34 will be subsequently deposited at the base of a user's male sex organ as part of the vacuum erection enhancement therapy using chamber 24, as understood by those of ordinary skill in the art without further discussion.

To facilitate transfer of an enlarged cincture band to the outside diameter of vacuum chamber 24, enlarged base 14 preferably defines an inwardly curved edge 36 for interfacing with an outwardly curved edge 38 of vacuum chamber entrance end 26. Struts 22 also preferably form outwardly curved surfaces 40, generally opposite the inwardly curved base edge 36, so as to collectively form with such edge 36 a generally semi-circular lip on the enlarged base. Such lip faces in a generally axial direction (with reference to axis 32 of present FIG. 1) for mating receipt of a corresponding generally semi-circular edge 38 of vacuum chamber entrance end 26. Where conical member 10 is used in association with an annular transfer collar, as discussed below with reference to FIGS. 3 through 5, it is generally preferred that such annular transfer collar also have a generally semi-circular edge for interfacing with the generally semi-circular lip of enlarged base 14. In either instance, the resulting at least small degree of overlap (with base 14 slightly surrounding in a circumferentially outward direction the outside diameter of the receiving object), even an enlarged resilient cincture band with considerable stored energy may be readily transferred to a vacuum chamber or annular transfer collar in accordance with this invention.

As discussed above, embodiments and usages of the present invention may include an annular transfer collar for temporarily receiving an enlarged resilient cincture band for its subsequent application to the base of a user's male sex organ. Present FIGS. 3 and 4 illustrate two presently preferred examples of such annular transfer collars 42 and 44. Each of such collars are preferably annular so that they might be slipped over the user's penis, whereafter an enlarged resilient constriction band carried about their outside diameter may be applied to the base of the user's penis. Present FIG. 5, discussed in greater detail below, illustrates receipt of an exemplary elastic constriction band 34 received about the outside diameter 46 of exemplary collar 42 (FIG. 3).

In general, entrance end 26 and respective entrance ends 48 and 50 of collars 42 and 44 have inside diameters which are the same. With such circumstances, a single set of struts or interference engagement means 22 may be adapted for alternate engagement with a vacuum chamber or annular transfer collar. An inside diameter 52 of approximately two inches is typical. While the outside diameter 54 of exemplary collar 44 may be substantially constant, exemplary collar 42 has a relatively reduced outside diameter region 56 at or adjacent an end 58 thereof opposite its end 48.

Figure 5:
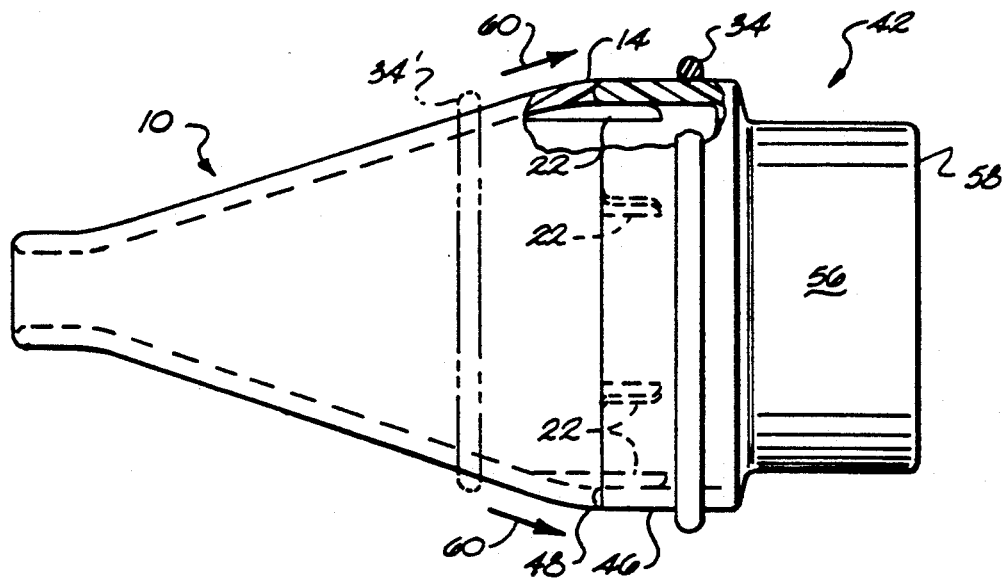
FIG. 5 is a side elevational view (with partial cross-sectional and dotted line illustration of certain features) of the present structures of FIGS. 2 and 3 associated in combination in accordance with one aspect of the present invention, and forming an embodiment thereof.

Present FIG. 5 illustrates a combination of conical member or cone means 10 with annular transfer collar 42. The inside diameter of region 46 is secured to cone means 10 with slight interference engagement of the plurality of struts 22, as discussed above. Also, the outside diameter of cone means 10 at its base 14 circumferentially surrounds the curved lip formed at edge 48 of collar 42. Accordingly, a resilient band 34' advanced in the direction of arrows 60 is readily transferred onto the outside diameter 46 of collar 42.

As represented in present FIG. 5, the relatively reduced outside diameter region 56 reduces the distance between the expanded condition of the elastic cincture band 34 and the diameter of the engorged male sex organ (not shown) to which it is to be applied. Such relative lessening of distance correspondingly results in less user discomfort upon transfer of such cincture band to the user's male sex organ. Such operations involve what is sometimes referred to as the "snap-down" effect. The alternate collar embodiment 42 of present FIG. 3 is particular advantageous for those users whose penis, when engorged, has a relatively smaller outside diameter. As should be understood by those of ordinary skill in the art, once elastic band 34 is received onto the outside diameter 46 of collar 42, it may be further advanced onto the relatively reduced outside diameter region 56, whereafter it is transferred to the base of such a user's male sex organ, with a resulting reduced "snap-down" effect.

Those of ordinary skill in the art will understand and appreciate that the engagement of conical member 10 with annular transfer collar 42 as effected by struts 22 is readily removable. Such removability facilitates transportation of annular member 42 (or annular member 44) to locations remote from conical member 10. Also, with such arrangement, an elastic band 34 may be preenlarged well prior to the time of need so that various manipulations involved with the present constriction band therapy will have less impact on the quality, nature, and spontaneity of the user's practices. Also, plural bands may be preenlarged onto a given annular transfer collar.

Modifications and variations as referenced above, and others, may be practiced. Those of ordinary skill in the art will further appreciate that the above disclosure is by way of example and description only, and is not intended as limiting the present invention, which is further set forth in the appended claims.

WHAT IS CLAIMED IS:

1. Apparatus for expanding an elastic penile cincture band to be subsequently applied to the outside diameter of a vacuum generating penile erection chamber or the base of a user's male sex organ, said apparatus comprising:
   a generally conical enlargement member having a relatively small diameter end and opposite thereto a relatively enlarged diameter base, with a tapered outside diameter between such end and such base; and
   a plurality of struts extending from said conical enlargement member base and adapted to alternatively engage the inside diameter of one of the entrance end of a vacuum generating penile erection chamber and a transfer collar for subsequent application to the base of a user's male sex organ so that an elastic penile cincture band may be readily expanded by its application against said tapered outside diameter and subsequently used to secure an engorged condition of a user's male sex organ.

2. An apparatus as in claim 1, wherein said enlargement member is generally hollow and comprised of plastic material.

3. An apparatus as in claim 2, further including openings defined in said end and said base to facilitate cleansing of said apparatus.

4. An apparatus as in claim 1, wherein said enlarged base defines an inwardly curved edge for interfacing with an outwardly curved edge of a vacuum chamber entrance end or a transfer collar.

5. An apparatus as in claim 4, wherein said plurality of struts form outwardly curved surfaces generally opposite said inwardly curved base edge, so as to collectively form with such edge a generally semi-circular lip on said enlarged base which faces in a generally axial direction for mating receipt of a corresponding generally semi-circular edge of a vacuum chamber entrance end or a transfer collar.

6. An apparatus as in claim 1, wherein said plural struts are adapted for removable interference engagement with a vacuum chamber entrance end or a transfer collar.

7. An apparatus as in claim 1, wherein said plurality of struts comprise six struts spaced generally equidistantly about said base.

8. Apparatus for expanding an elastic penile cincture band to be subsequently applied to the outside diameter of a vacuum generating penile erection chamber or the base of a user's male sex organ, said apparatus comprising:
   a generally conical enlargement member having a relatively small diameter end and opposite thereto a relatively enlarged diameter base, with a tapered outside diameter between such end and such base;
   a plurality of struts extending from said conical enlargement member base and adapted to engage the inside diameter of a transfer collar for subsequent application to the base of a user's male sex organ; and
   an annular transfer collar with at least one end thereof adapted for removable interference engagement with said plurality of struts for temporary association of said annular transfer collar with said enlargement member so that a penile cincture band ay be expanded and transferred onto said annular transfer collar, after which said annular collar may be separated from said enlargement member with an expanded resilient penile cincture band thereabout and applied over a user's male sex organ for placement of such cincture band at the base of a user's engorged male sex organ so as to secure an engorged condition of such male sex organ.

9. An apparatus as in claim 8, wherein said annular transfer collar has a substantially constant outside diameter.

10. An apparatus as in claim 8, wherein said annular transfer collar has a relatively reduced outside diameter region at an end thereof opposite said at least one end thereof, for reducing the distance between the expanded condition of the elastic cincture band and the diameter of the engorged male sex organ to which it is to be applied so as to lessen user discomfort upon transfer of such cincture band to the user's male sex organ.

11. A device for expanding an elastic penile cincture band and facilitating transfer of the expanded band to a further structure for subsequent use in securing ann engorged condition of the user's penis, said device including:
   cone means, having a tapered end and a relatively enlarged circular base which terminates in a curved and generally axially facing lip, for expanding a resilient penile cincture band applied to said tapered end thereof and advanced towards said relatively enlarged circular base; and
   interference engagement means, supported on said cone means and projecting generally axially therefrom, for removably engaging said cone means with a further structure such as a penile vacuum chamber or an annular transfer collar, with such structure having an engagement edge thereof received against said cone means axially facing lip, so that a resilient penile cincture band may be readily expanded by said cone means and transferred to a further structure temporarily associated therewith by said interference engagement means; and wherein said interference engagement means comprise a plurality of support struts attached to the interior of said cone means.

12. A device as in claim 11, wherein said cone means is generally hollow and comprised of plastic material.

13. A device as in claim 12, wherein said cone means further includes openings defined in said end and said base thereof to facilitate cleansing of said cone means.

14. A device as in claim 1, wherein said plural struts comprise six struts spaced generally equi-distantly about said cone means base.

15. A device for facilitating expansion of a resilient penile cincture band and subsequent transference thereof to the base of a user's penis for securing an engorged penile condition, comprising:
  a hollow conical member having a relatively enlarged circular base tapering in an axial direction of said member to a relatively smaller end, with openings defined in said base and said end to facilitate cleansing of said member interior, and further having a curved, axially facing engagement lip defined in said circular base;
  a plurality of engagement members integrally formed with the interior of said hollow conical member and extending in a generally axial direction from said base thereof; and
  an annular transfer collar having an inside diameter adapted for a removable interference fit about said engagement members, and having a curved engagement edge adapted for fitting to said conical member circular base engagement lip so that a resilient cincture band slipped over said conical member relatively smaller end and advanced towards said base thereof may be expanded for transfer to said annular transfer collar, whereafter said collar may be selectively removed from said interference fit with said engagement members with the expanded band thereabout and slipped over a user's penis for securement of an engorged condition thereof by applying the expanded band to the base of the penis.

16. A device as in claim 15, wherein said annular transfer collar has a relatively reduced outside diameter portion for reducing the requisite contraction distance of the expanded band during its application to the user's penis, thereby reducing discomfort to the user during such application.

17. A device as in claim 15, wherein said engagement members, whenever separated from said annular transfer collar, are adapted for forming a removable interference fit with the entrance end of a penile vacuum chamber so that a cincture band may be expanded and transferred directly to the outside diameter of such vacuum chamber for subsequent application to the base of a user's penis to secure an engorged condition thereof obtained with such vacuum device.

* * * * *